US011930996B2

(12) United States Patent
Dresher

(10) Patent No.: US 11,930,996 B2
(45) Date of Patent: *Mar. 19, 2024

(54) SIGNAL TRANSMISSION COMPONENTS FOR USE WITH MEDICAL DEVICES

(71) Applicant: Boston Scientific Scimed, Inc., Maple Grove, MN (US)

(72) Inventor: Russell Dresher, Hudson, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 647 days.

This patent is subject to a terminal disclaimer.

(21) Appl. No.: 17/107,459

(22) Filed: Nov. 30, 2020

(65) Prior Publication Data

US 2021/0076908 A1 Mar. 18, 2021

Related U.S. Application Data

(63) Continuation of application No. 15/590,324, filed on May 9, 2017, now Pat. No. 10,874,283, which is a (Continued)

(51) Int. Cl.
*A61B 1/00* (2006.01)
*A61B 1/012* (2006.01)
(Continued)

(52) U.S. Cl.
CPC ...... *A61B 1/00018* (2013.01); *A61B 1/00114* (2013.01); *A61B 1/012* (2013.01);
(Continued)

(58) Field of Classification Search
CPC . A61B 1/00018; A61B 1/00114; A61B 1/012; A61B 1/05; A61B 5/7217
See application file for complete search history.

(56) References Cited

U.S. PATENT DOCUMENTS 5,402,769 A 4/1995 Tsuji
5,569,158 A 10/1996 Suzuki et al.
(Continued)

FOREIGN PATENT DOCUMENTS

CN 2591789 Y 12/2003
CN 101645325 A 2/2010
(Continued)

OTHER PUBLICATIONS

Invitation to Pay Additional Fee and, Where Applicable, Protest Fee and Partial International Search Report for corresponding international application PCT/US2013/053402, dated Jan. 7, 2014, 4 pages.

*Primary Examiner* — Timothy J Neal
*Assistant Examiner* — William B Chou
(74) *Attorney, Agent, or Firm* — Bookoff McAndrews, PLLC

(57) ABSTRACT

Embodiments of the present disclosure relate to a medical device. The medical device may include an elongate member, having a proximal end and a distal end and at least two lumens extending therebetween. At least one of the lumens may be an imaging lumen configured to hold an imaging device, and an imaging device may be disposed inside the imaging lumen. A signal transmitting device may extend longitudinally through the imaging lumen. A distal end of the signal transmitting device may be operably coupled to the imaging device and a proximal end may be operably coupled to a processor. The processor may be located outside of the imaging lumen. The signal transmitting device may transmit signals between the imaging device and the processor. A grounded, braided catheter may be disposed within and extend the length of the elongate member, surrounding the imaging lumen.

19 Claims, 5 Drawing Sheets

Related U.S. Application Data continuation of application No. 14/059,128, filed on Oct. 21, 2013, now Pat. No. 9,675,233.

(60) Provisional application No. 61/717,349, filed on Oct. 23, 2012.

(51) Int. Cl.
    *A61B 1/05* (2006.01)
    *A61B 1/07* (2006.01)
    *A61B 5/00* (2006.01)

(52) U.S. Cl.
    CPC .............. *A61B 1/05* (2013.01); *A61B 5/7217* (2013.01); *A61B 1/07* (2013.01)

(56) References Cited

U.S. PATENT DOCUMENTS

| | | |
|---|---|---|
| 5,810,714 A | 9/1998 | Takamura et al. |
| 6,288,337 B1 | 9/2001 | Sato et al. |
| 6,319,197 B1 | 11/2001 | Tsuji et al. |
| 6,740,808 B1 | 5/2004 | Chang |
| 9,620,262 B1 | 4/2017 | Salz |
| 2006/0025651 A1 | 2/2006 | Adler et al. |
| 2006/0114986 A1 | 6/2006 | Knapp, II et al. |
| 2008/0051634 A1 | 2/2008 | Yamashita |
| 2008/0146943 A1 | 6/2008 | Jenkins et al. |
| 2010/0084157 A1 | 4/2010 | Wang |
| 2010/0280584 A1 | 11/2010 | Johnson et al. |
| 2011/0220389 A1 | 9/2011 | Huang et al. |
| 2011/0301414 A1 | 12/2011 | Hotto et al. |
| 2012/0143180 A1 | 6/2012 | Lee et al. |
| 2012/0199376 A1 | 8/2012 | Konya |
| 2013/0072041 A1 | 3/2013 | Nonen et al. |
| 2013/0087361 A1 | 4/2013 | Kaga et al. |
| 2013/0303920 A1 | 11/2013 | Corl |
| 2014/0012130 A1 | 1/2014 | Jacobsen et al. |
| 2014/0371736 A1 | 12/2014 | Levin et al. |
| 2015/0094914 A1 | 4/2015 | Abreu |
| 2016/0008050 A1 | 1/2016 | Rajagopalan et al. |

FOREIGN PATENT DOCUMENTS

| | | |
|---|---|---|
| CN | 101108117 A | 1/2018 |
| EP | 0 730 844 A1 | 9/1996 |
| JP | 2003210463 A | 7/2003 |

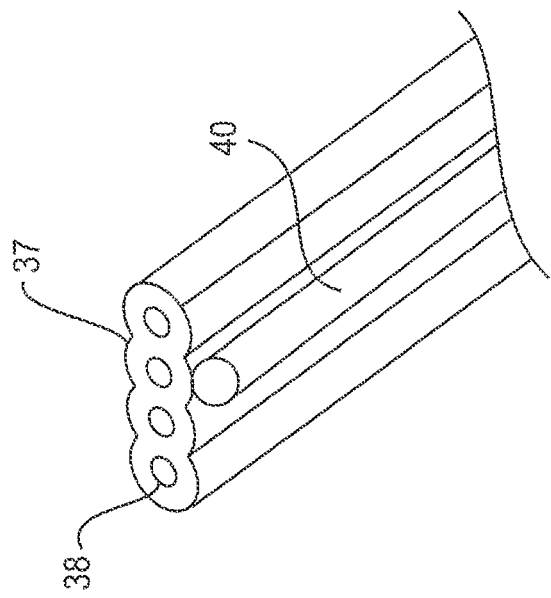
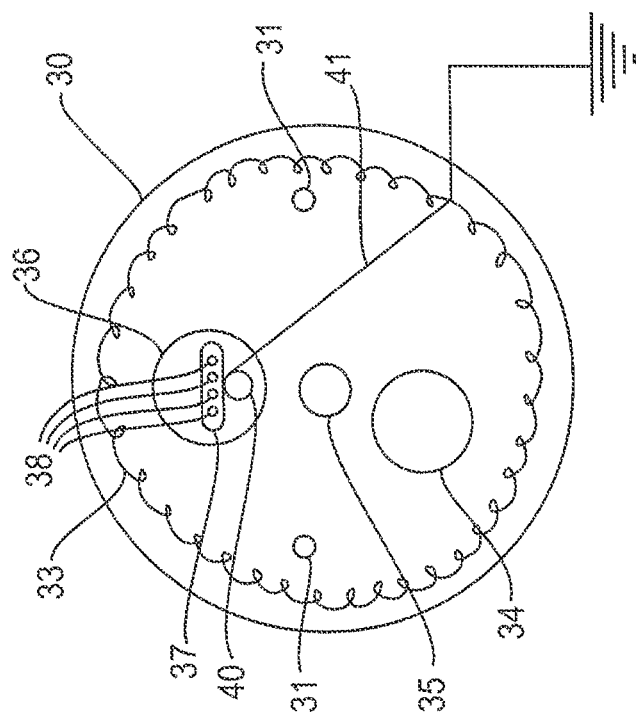

SIGNAL TRANSMISSION COMPONENTS FOR USE WITH MEDICAL DEVICES

CROSS-REFERENCE TO RELATED APPLICATIONS

This application is a continuation of U.S. application Ser. No. 15/590,324, filed May 9, 2017, which is a continuation of U.S. application Ser. No. 14/059,128, filed Oct. 21, 2013, now U.S. Pat. No. 9,675,233, which claims the benefit of priority from U.S. Provisional Application No. 61/717,349, filed on Oct. 23, 2012, all of which are incorporated herein by reference in their entireties.

FIELD OF THE DISCLOSURE

The present disclosure relates generally to medical devices and systems. More particularly, embodiments of the disclosure relate to noise reduction components for use with electronic endoscopes, including, for example, endoscopes that are part of a medical imaging system.

BACKGROUND OF THE DISCLOSURE

Electrically charged objects, such as, for example, electrical medical equipment, may generate electromagnetic (EM) fields. EM fields may affect the behavior of other charged objects in the vicinity. Mathematical relationships, such as Maxwell's and Faraday's equations and the Lorentz force law, demonstrate that radiated EM fields can induce electric currents on nearby equipment. These induced currents are generally referred to as electromagnetic interference (EMI), and they may interfere with or corrupt electrical signals generated by nearby medical equipment. In a medical setting, such as an operating room or a physician's office, electrical equipment may generate EM fields that affect other medical instrumentation in the vicinity. While medical equipment may be regulated and tested according to industry standards in order to limit the magnitude of EM fields produced, EM fields and radiation may also be generated by other equipment present in a medical facility.

In the case of a digital endoscope, electrical equipment, such as imaging systems, including cameras located on a distal region for viewing an internal region, may be affected by such EM fields. The EM fields generated by surrounding equipment may couple with cables associated with a digital endoscopic camera, corrupting signals relayed to and from the camera. EM fields may also couple with electronic cables connecting distal endoscopic components, like the digital camera, to proximal electronics, for example, an imaging processor. Additionally, any other electrical components placed near the EM source may be corrupted.

This corruption from stray current, sometimes referred to as "airborne EMI," may have a detrimental effect on endoscopic medical equipment. Cables connecting the distal and proximal electronics of an endoscope may be particularly susceptible to corruption, because the conductors within the cables may act as long antennae, attracting electrical noise from the EM field. These cables may transmit video signal from a distally located endoscopic camera to proximal video processing equipment. In the case of endoscopic imaging equipment, the coupled EMI may corrupt video signal, causing image degradation or, in some instances, complete loss of video imaging. Thus, there exists a need to reduce EM field noise coupling to endoscopic cabling.

One method of reducing the effects of coupling from airborne EMI to endoscopic cables involves twisting the individual cable conductors together. Twisting the conductors may uniformly expose each conductor to substantially the same noise. Electronic hardware and/or software may then be able to detect the similar signal components, i.e. noise, across each individual cable conductor, allowing the hardware and software to subtract that noise uniformly from the total signal output. However, twisting conductors or conductor pairs may not always be feasible. For example, some medical devices, such as endoscopes, may have size constraints to allow them to navigate narrow body lumens. Because twisting conductors may add additional bulk to the cables, this method of noise reduction may not be possible for some devices.

Another noise-reduction technique includes surrounding noise-sensitive cables with an EMI shield. Such shields may include, e.g., copper tape or EMI shielding paint, which may be painted on the cabling enclosure, for example. Adding EMI shielding may increase the cost of such devices, however, which is a concern particularly for disposable endoscopes. In some cases, the addition of an EMI shield may be difficult or impossible. For example, it may not be possible to coat the internal lumen of a catheter with EMI shielding paint.

Noise coupling may also occur through a conductive medium, for example, saline or bodily fluid. This source of noise coupling may be referred to as "conductively coupled noise," For example, if an electrical signal is applied to a volume of saline solution, a resulting signal can be measured on an electrode placed in contact with the saline. The saline acts as a conductive path, allowing the injected signal to couple with the electrode. For a medical device, such as an endoscope, bodily fluid or saline used for irrigation, for example, may surround portions of the internal electronic cabling when the endoscope is exposed to such fluidic environments. The conductivity of this fluid medium thus increases the potential for noise coupling between the fluid and the cables.

One method of decreasing conductively coupled noise is to reduce the amount of fluid in contact with the cabling. Placing the cabling in a separate, sealed lumen may prevent fluids from contacting the cabling. Yet, the size constraints of endoscopes may make sealing the cables difficult. For example, a wall between a visualization lumen of an endoscope and an irrigation and/or aspiration lumen may be thin, for example, to reduce size or increase flexibility. Consequently, the thin wall may be prone to processing defects and/or mechanical damage during a medical procedure. These defects may allow fluid from the irrigation and/or aspiration lumen to enter into the visualization lumen. When an electronic imaging endoscope is used, fluid may surround an electrical cable disposed in the visualization lumen and may fill available space between adjacent conductors of the electronic cable assembly. This may result in imaging signal degradation or failure. Additionally, manufacturing thin walls capable of increased fluid impermeability may also increase the cost of medical devices.

Another method of reducing conductively coupled noise is to electrically insulate the signal conductors using insulation around the cable. However, the insulation must be of sufficient thickness to prevent noise from coupling to the internal conductors. As a result, using insulation may add to the space requirements of a medical device and therefore may not be feasible for use in smaller-diameter devices, such as endoscopes. Accordingly, a need exists for a means of insulating cables from environmental noise and/or fluid without increasing space requirements, decreasing flexibility, or increasing the cost of a digital imaging endoscope.

SUMMARY

Embodiments of the present disclosure are directed to a medical device. The medical device may include an elongate member, having a proximal end and a distal end and at least two lumens extending therebetween. At least one of the lumens may be an imaging lumen configured to hold an imaging device, and an imaging device may be disposed inside the imaging lumen. A signal transmitting device may extend longitudinally through the imaging lumen. A distal end of the signal transmitting device may be operably coupled to the imaging device and a proximal end may be operably coupled to a processor. The processor may be located outside of the imaging lumen. The signal transmitting device may transmit signals between the imaging device and the processor. A grounded, braided catheter may be disposed within and extend the length of the elongate member, surrounding the imaging lumen.

In various embodiments, the medical device may include one or more of the following additional features: the imaging device may be a camera; the signal transmitting device may be a cable; the braided catheter may completely surround the circumference of the imaging lumen; the medical device may include an illumination lumen configured to house an illumination device, and an illumination device disposed within the illumination lumen; the braided catheter may completely surround the circumferences of both the illumination lumen and the imaging lumen; the braided catheter may be formed of a conductive material; the braided catheter may be connected to a floating ground or an earth ground; the medical device may include an antenna disposed within the elongate member and extending the length of the signal transmitting device; the antenna may be disposed within the imaging lumen; the antenna may be located adjacent to the signal transmitting device; the antenna may be formed of a conductive material and may be electrically grounded; and the antenna may be connected to the same ground as the braided catheter.

Further embodiments of the disclosure are directed to a medical device. The medical device may include an elongate member, having a proximal end and a distal end and at least two lumens extending therebetween. At least one of the lumens may be an imaging lumen configured to hold an imaging device, and an imaging device may be disposed inside the imaging lumen. At least one cable may extend longitudinally through the imaging lumen. A distal end of the at least one cable may be operably coupled to the imaging device and a proximal end may be operably coupled to a processor. The processor may be located outside of the imaging lumen. The at least one cable may transmit signals between the imaging device and the processor. The medical device may also include a non-conductive medium disposed in the imaging lumen and surrounding the cable.

In various embodiments, the medical device may include one or more of the following additional features: the non-conductive medium may be a fluid having a density higher than water and the fluid may be sealed within the imaging lumen; the medical device may include a grounded, braided catheter disposed within the elongate member and surrounding the circumference of the imaging lumen; the medical device may also include a conductive antenna adjacent to the cable and extending the length of the cable.

Another embodiment of the disclosure relates to a medical device having an elongate member with a proximal end and a distal end and an imaging lumen extending therebetween. An imaging device may be disposed in the imaging lumen. At least one cable may be disposed within the imaging lumen. A distal end of the at least one cable may operably couple the imaging device and a proximal end may operably couple a processor. The at least one cable may transmit signals between the imaging device and the processor. The medical device may also include a conductive antenna extending the length of the at least one cable within the imaging lumen. The medical device may also include a braided catheter extending the length of the elongate member and disposed between an exterior wall of the elongate member and an exterior wall of the imaging lumen. The braided catheter may surround the circumference of the imaging lumen. The braided catheter and the antenna may be connected to an electrical ground.

In various embodiments, the braided catheter and the antenna may be configured to attract current from an electromagnetic field to provide a low-impedance pathway to the ground.

Additional objects and advantages of the embodiments will be set forth in part in the description that follows, and in part will be obvious from the description, or may be learned by practice of the embodiments. The objects and advantages of the invention will be realized and attained by of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 5A illustrates an exemplary transverse cross-sectional view of an endoscope, according to an embodiment of the present disclosure; and FIG. 5B illustrates a perspective view of the electronic cable assembly of the endoscope illustrated in FIG. 5A.

DESCRIPTION OF THE EMBODIMENTS

Reference will now be made in detail to the exemplary embodiments of the present disclosure described below and illustrated in the accompanying drawings. Wherever possible, the same reference numbers will be used throughout the drawings to refer to same or like parts.

While the present disclosure is described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents that all fall within the scope of the invention. Accordingly, the disclosure is not to be considered as limited by the foregoing or following descriptions.

Other features and advantages and potential uses of the present disclosure will become apparent to someone skilled in the art from the following description of the disclosure, which refers to the accompanying drawings.

Figure 1:
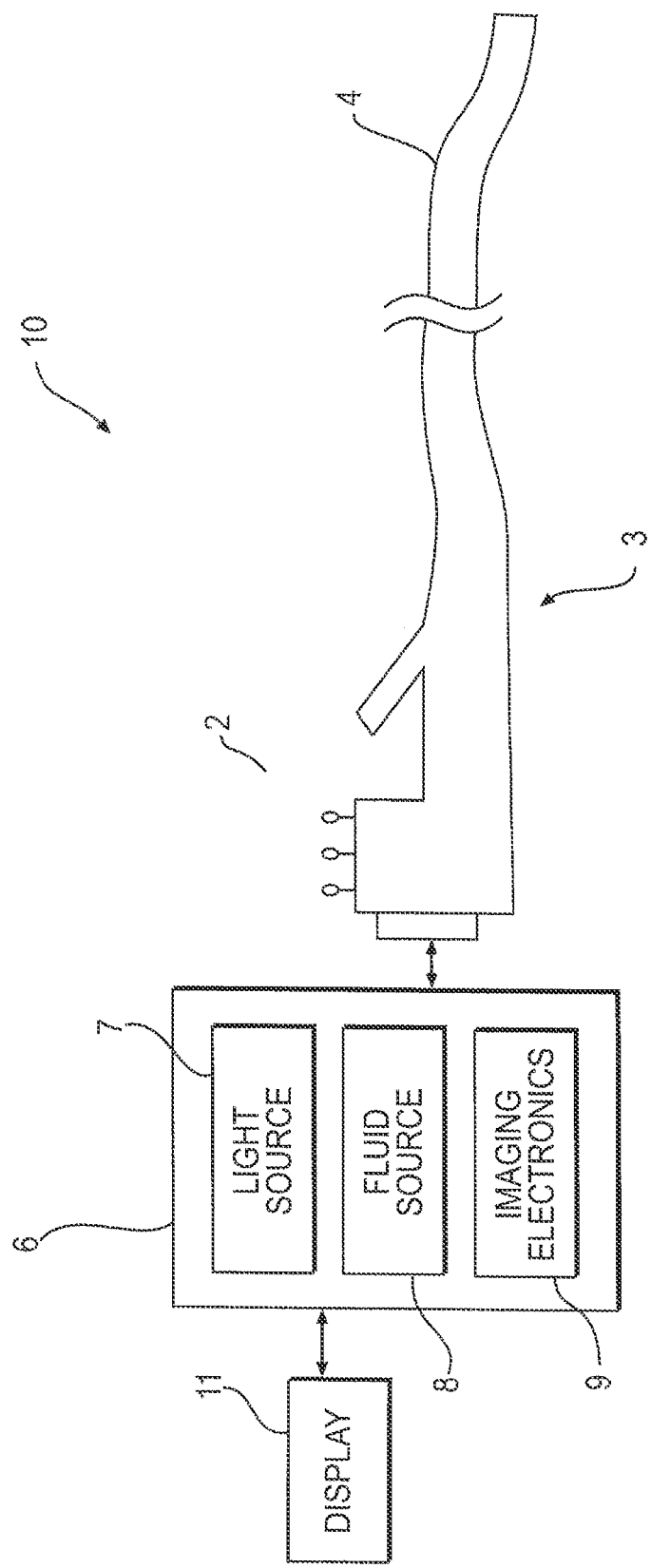
FIG. 1 illustrates an exemplary medical imaging system, according to an embodiment of the present disclosure.

FIG. 1 illustrates an exemplary medical imaging system 10 and related components. The exemplary medical imaging system 10 may be used for therapeutic, observational, and/or diagnostic procedures. The term "medical imaging system" is used broadly to include all components and systems that may be used during a medical procedure.

Medical imaging system 10 may include an endoscope 3 configured for insertion into the body of a patient. While the disclosure refers to an endoscope, any suitable introduction sheath may be used, for example, a catheter, a guide tube, a trocar, a ureteroscope, a colonoscope, a laparoscope, or any suitable medical device. Endoscope 3 may be inserted into the body through any suitable opening, for example, a natural opening, surgical incision, or percutaneous opening. In the exemplary embodiment, medical imaging system 10 may also include a control unit 6, a display 11 operably connected to control unit 6, and endoscope 3 operably connected to control unit 6. Any suitable number or assortment of components may be included in medical imaging system 10. The components may be connected to one another or may be connected only to control unit 6. Such connections may be wireless or physical, or a combination of the two. Control unit 6 may include one or more devices, for example, a light source 7, imaging electronics 9, and a fluid source 8. Control unit 6 may include any number or combination of suitable devices, including, but not limited to, data storage or processing, sensors or sensor feedback processing, steering controllers, and data input systems. These devices may be provided together in a single console or may be separately provided.

Endoscope 3 may be an electronic endoscope configured to allow a clinician to view internal body cavities of a patient and may be configured for insertion into narrow and/or tortuous body lumens. Endoscope 3 may be a disposable, single-use endoscope or may be reusable.

Endoscope 3 includes a proximal end, a distal end, and an elongate member 4 extending between the proximal and distal ends. For purposes of this disclosure, "proximal" refers to the end closer to the device operator during use, and "distal" refers to the end further from the device operator during use.

Elongate member 4 extends distally from a handle portion 2. Endoscope 3 may be rigid or flexible, or may have both flexible and rigid portions. Elongate member 4 may be formed of any suitable biocompatible material known to one of ordinary skill in the art. Such materials may include, but are not limited to, rubber, silicon, synthetic plastic, stainless steel, metal-polymer composites, and metal alloys of nickel, titanium, copper, cobalt, vanadium, chromium, aluminum, tantalum, and iron. In one embodiment, the material forming elongate member 4 may be a super-elastic or shape-memory material such as nitinol, which is a nickel-titanium alloy. Elongate member 4 may have any cross-sectional shape and/or configuration, and may be any dimension capable of being received in an endoscope, guide, or body cavity. Endoscope 3 and/or elongate member 4 may be steerable and may have areas of different flexibility or stiffness (e.g., to promote steerability).

Figure 2:
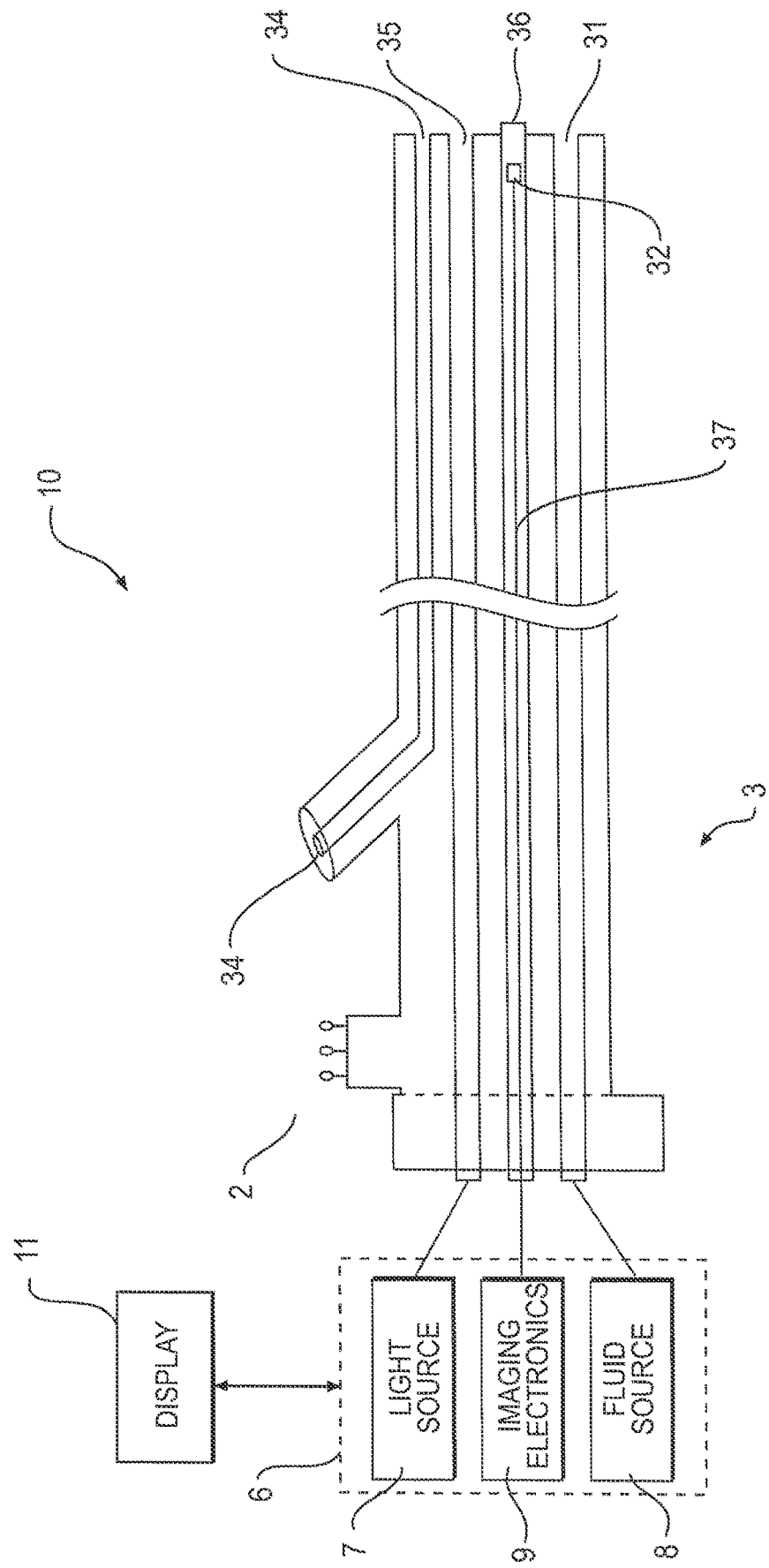
FIG. 2 illustrates a longitudinal cross-sectional view of an endoscope component of the exemplary medical imaging system depicted in FIG. 1.

As depicted in FIG. 2, endoscope 3 and/or elongate member 4 may include one or more lumens extending between the proximal end and the distal end. Endoscope 3 may include, for example, a working lumen 34, an illumination lumen 35, an imaging lumen 36 and irrigation or aspiration lumens 31. The number, type, size, cross-sectional shape, and orientation of lumens may vary depending on the type of endoscope used or the type of procedure performed, and any suitable configuration of lumens may be used. Additionally, the lumens may be configured to receive various types of components, examples of which are described in more detail below. One or more lumens may be configured to movably receive various components, such as medical instruments or sensors, e.g., while some lumens may be configured to permanently house certain components. Some components may be configured to extend beyond a distal end of endoscope 3, while other components may remain housed within an interior region of a lumen. Each lumen may house one device, or may house multiple devices or no devices.

Working lumen 34 may be configured to receive one or more medical instruments to guide the medical instruments to a working site within the body of a patient. Working lumen 34 may receive any suitable medical instrument, for example, a grasper, forceps, scissors, basket, cutting device, probe, or sensor. The medical instrument may or may not be configured to receive electrical current. One or more irrigation lumens 31 may be configured to deliver fluids, e.g., gas or liquids, from fluid source 8 to tissue adjacent the distal region of endoscope 3. In some embodiments, irrigation lumen 31 may be configured to suction fluid from a work site back into fluid source 8.

Illumination lumen 35 and imaging lumen 36 may be connected to and/or configured to receive suitable electrical imaging components. For example, illumination lumen 35 may be configured to receive an illumination device (not shown) to illuminate tissue adjacent a distal end of endoscope 3. The illumination device may be operably coupled to light source 7, which may include one or more light-emitting diodes or electrical filaments, for example, via an optical fiber or fiber bundle (not shown) extending through illumination lumen 35. In some embodiments, a fiber optic cable or light pipe may extend through Illumination lumen 35 and may connect to light source 7.

An imaging device 32 may be disposed at a distal region of imaging lumen 36. Imaging device 32 may include, for example, a camera for capturing still or moving images, a lens, a digital imaging chip, or other image-receiving devices, which may transmit signals in an analog or digital format via cable 37. In an exemplary embodiment, imaging device 32 may include an image sensor, such as a CMOS imaging sensor, CCD, or other solid state device, and one or more lenses capable of producing electronic imaging signals. An exemplary imaging sensor may be configured for low light and/or low noise levels.

One or more electronic cables 37 may operably connect one or more imaging devices 32 to proximal imaging electronics 9. Electronic cable 37 may transmit imaging signals from imaging device 32 to, for example, a processor, a memory storage device, and/or a display 11. Signals relayed from imaging device 32 may directly transmit raw images to display 11, or the imaging signals may be processed first and then displayed. One or more displays 11 may be incorporated into control unit 6, or may be separate from control unit 6, for example at a separate location in the sale soon or in a location remote control unit 6 and/or endoscope 3. Display 11 may be wirelessly or physically coupled to control unit 6. In some embodiments, imaging electronics 9 may also transmit a control signal to imaging device 32 via cable 37 to control various aspects of operation. For example, imaging electronics 9 may control or adjust the movement, location, aperture size, shutter speed, zoom, or any other operation of imaging device 32. Imaging electronics 9 may also be coupled to light source 7 or an illumination component in illumination lumen 35 to control the amount of light provided for imaging device 32.

Figure 3:
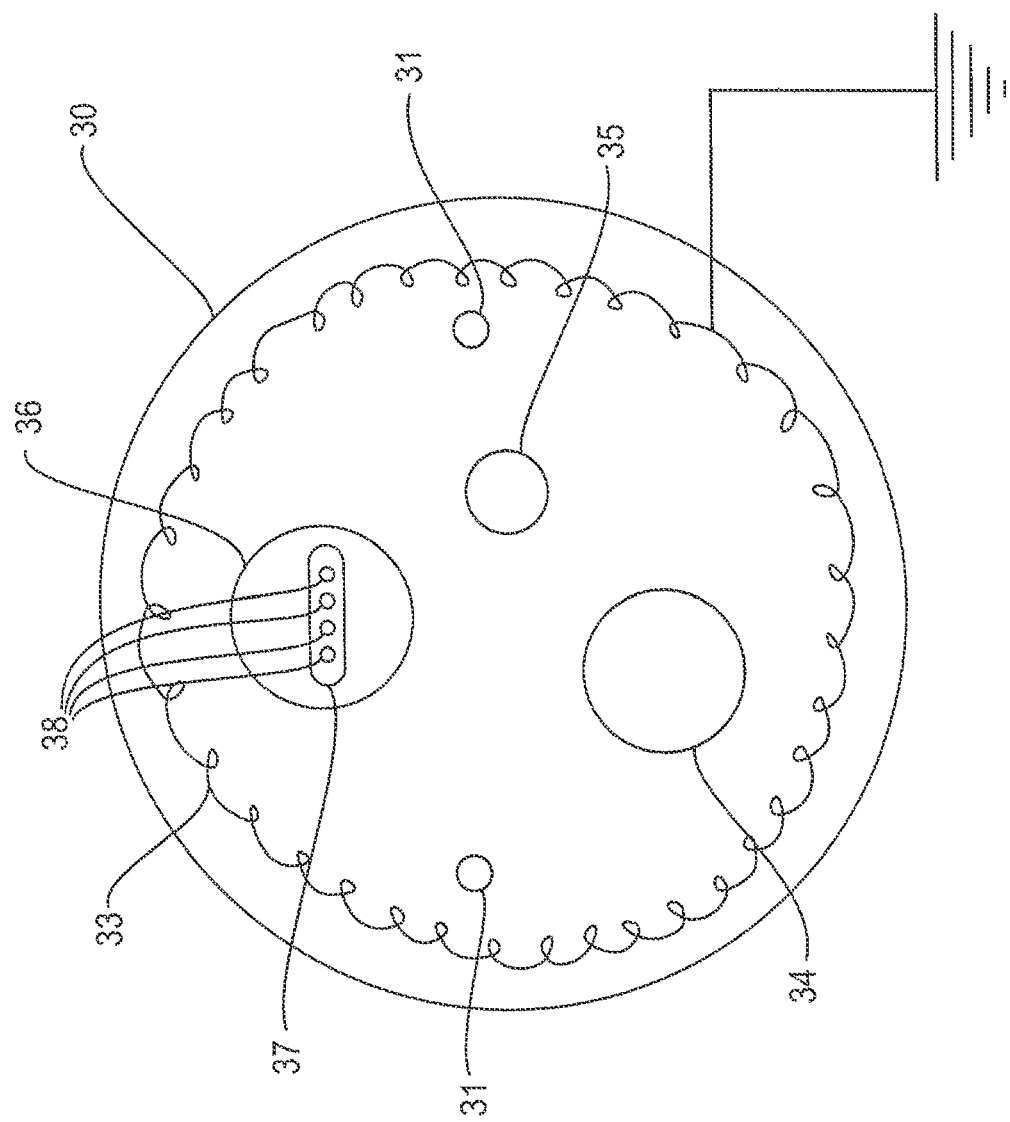
FIG. 3 illustrates an exemplary transverse ross-sectional view of an endoscope, according to an embodiment of the present disclosure.

Cable 37 may be comprised of one or more conductors 38, as shown in FIG. 3. In one embodiment, conductors 38 may be fine gage conductors between approximately 30 and 50 gage, for example. Conductors 38 may be formed of any suitable conductive, biocompatible material, e.g., metals, alloys, polymers, carbon, or any combination thereof. In the depicted exemplary embodiments, conductors 38 have a circular cross-section, however, conductors 38 may have any suitable cross-sectional shape, for example, rectangular or oval. Conductors 38 may be contained within insulation to form one cable. The exemplary figures depict one cable 37 with four conductors 38 arranged in linear fashion, but any suitable number of cables or configuration of conductors may be used. For example, conductors 38 may be twisted or may be arranged in a concentric our clustered configuration.

The insulation surrounding conductors 38 of cable 37 may be configured to exclude fluid when endoscope 3 is exposed to a fluidic environment. For example, the insulation material may completely surround each conductor 38 and may substantially fill any gaps between adjacent conductors 38. The insulation may be formed of any suitable material, for example rubber, silicone, polyurethane, ethylene, tertrafluoroethylene, polytetrafluoroethylene, polydimethylsiloxane, or any other non-conductive, biocompatible material.

As discussed above, airborne EMI and/or conductively coupled noise may affect cable 37, corrupting the imaging signals transmitted from imaging device 32 to imaging electronics 9. To reduce coupling caused by airborne EMI, elongate member 4 of endoscope 3 may include a braided or mesh catheter 33. Braided catheter 33 may form an outer layer of elongate member 4, or braided catheter 33 may be housed within an outer layer 30 of elongate member 4, as depicted in FIG. 3. Braided or mesh catheter 33 may be formed of a suitable material for EMI shielding, e.g., stainless steel, copper, or a super-elastic or shape-memory alloy, such as nitinol, for example. Braided catheter 33 may also provide structural support for elongate member 4 and may improve the steering and/or ability to push elongate member 4 through a body cavity.

Braided catheter 33 may surround and enclose electronic cable 37 to substantially isolate the cabling from the surrounding environment to reduce the coupling effect of EM fields. Thus, braided catheter 33 may completely encircle electronic cable 37 and/or electronic components contained in imaging channel 36 and may extend along a length of elongate member 4. The material, thickness, size, and location of braided catheter 33 may be varied to adjust the amount of noise reduction from airborne coupling.

Braided catheter 33 may be connected to a low impedance path to ground, as shown in FIG. 3. In some embodiments, braided catheter 33 may remain connected to a floating, signal ground or an earth ground. Grounding braided catheter 33 may increase patient safety by reducing the risk that stray electrical current contacts the patient. Braided catheter 33 may reduce airborne EMI in a cost-effective manner without substantially increasing the number of components or the size requirements of elongate member 4.

Figure 4:
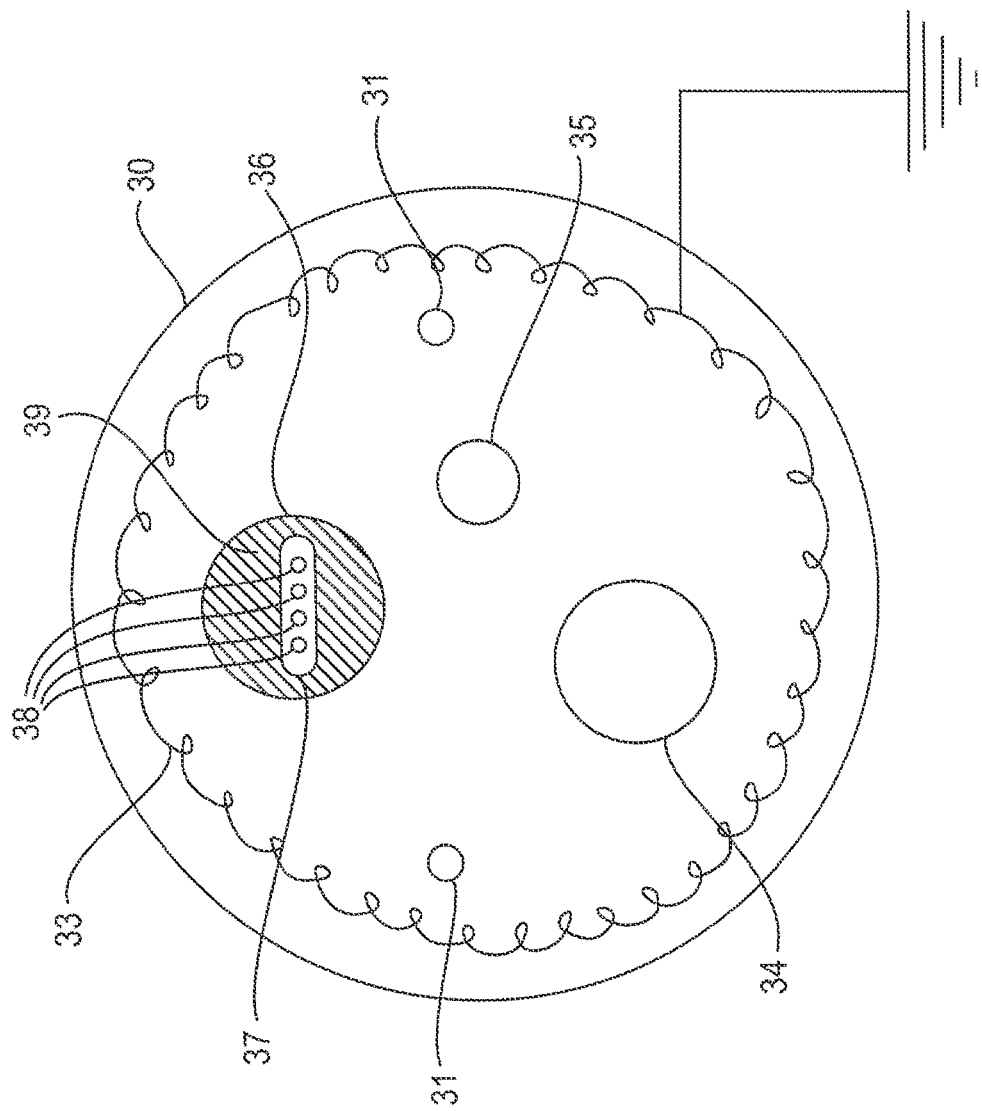
FIG. 4 illustrates another exemplary transverse cross-sectional view of an endoscope, according to an embodiment of the present disclosure.

In one embodiment, a non-conductive medium may be used instead of, or in addition to, braided catheter 33 to reduce airborne EMI or conductively coupled noise. As shown in FIG. 4, a nonconductive medium 39 may be used to surround, seal, or fill an area surrounding cable 37. For example, imaging lumen 36 may contain non-conductive medium 39 surrounding cable 37 and/or a portion of imaging unit 32 (shown in FIG. 2). Non-conductive medium 39 may have a higher density than surrounding fluids, such as saline from one or more irrigation lumens 31 or bodily fluids, like blood or urine. While non-conductive medium 39 may decrease noise coupling, its higher density may reduce the likelihood that conductive fluids will mix with the non-conductive medium. Any suitable liquid or solid non-conductive medium may be used to surround cable 37, for example, oils or other biocornpatible mediums. If a fluid non-conductive medium 39 is used, seals and other components may be used to prevent medium 39 from leaking into the patient's body or into other regions of endoscope 3.

In one embodiment, an additional component, such as an antenna may be used to pick up noise, reducing the likelihood that such noise couples to cable 37. As discussed above, cable 37 connecting the distal and proximal electronics of an endoscope may be particularly susceptible to corruption, because the conductors within the cable may act as long antennaes, attracting electrical noise from the EM field. Providing an antenna near cable 37 may redirect the stray current and couple EMI to itself instead of coupling to conductors 38 of cable 37.

For example, as depicted in FIGS. 5A and 53, antenna 40 may be situated near cable 37 and may extend the length of cable 37. One or more antennae 40 may extend near or adjacent to one or more cables 37 and may run parallel to or may wrap around one or more cables 37. Antenna 40 may be situated near any electrical component in endoscope 3 to re-direct conductively coupled noise or airborne EMI from the electrical component to antenna 40, decreasing the likelihood of signal corruption. Antenna 40 may be formed of any suitable conductive, biocompatible material, e.g., metals, alloys, polymers, carbon, or any combination thereof. In the depicted exemplary embodiments, antenna 40 has a circular cross-section, however, antenna 40 may have any suitable cross-sectional shape, for example, rectangular or oval and may take any suitable shape, for example, a conductive wire or a wire wrap.

Antenna 40 may be grounded to promote patient safety. If used in conjunction with braided catheter 33, described above, antenna 40 may be coupled to the same ground as braided catheter 33. Noise coupled to saline or bodily fluid may couple to the antenna, which may then provide a low impedance path to ground. Accordingly, noise may couple to antenna 40 instead of cable 37. Antenna 40 may have a reduced diameter so as to reduce manufacturing costs and/or reduce the amount of space required inside endoscope 3. When used alone or when used in conjunction with braided catheter 33, antenna 40 may reduce both airborne EMI and conductively coupled noise, thus reducing imaging signal corruption in potentially noisy environments, such as medical imaging system 10.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the claims are not to be considered as limited by the foregoing description.

What is claimed is:

1. A medical device, comprising:
    a shaft member having a first lumen and a second lumen each extending longitudinally therein;
    at least one cable extending through the first lumen, the at least one cable including:
        at least one conductor extending longitudinally through the first lumen for transmitting electronic data, and
        an insulator surrounding the at least one conductor;
    a conductive wire disposed within the first lumen; and
    an electromagnetic interference shielding catheter extending along the shaft member, surrounding the first lumen and surrounding the second lumen,
    wherein the conductive wire and the electromagnetic interference shielding catheter are electrically coupled.

2. The medical device of claim 1, wherein the shaft member includes an outer layer, and wherein the electromagnetic interference shielding catheter is embedded within the outer layer.

3. The medical device of claim 1, wherein the electromagnetic interference shielding catheter includes a braided catheter or a mesh catheter.

4. The medical device of claim 1, wherein the at least one cable lies between the conductive wire and the electromagnetic interference shielding catheter.

5. The medical device of claim 4, wherein the first lumen is an imaging lumen and the second lumen is a working lumen, and wherein the conductive wire lies between the at least one cable and the working lumen.

6. The medical device of claim 4, wherein the conductive wire and the electromagnetic interference shielding catheter are connected to a same ground.

7. The medical device of claim 1, wherein the electromagnetic interference shielding catheter is connected to at least one of a floating ground, a signal ground, or an earth ground.

8. The medical device of claim 1, further comprising at least one of an irrigation lumen or an illumination lumen.

9. The medical device of claim 8, further comprising both the irrigation lumen and the illumination lumen, and wherein the electromagnetic interference shielding catheter further surrounds the irrigation lumen and the illumination lumen.

10. A medical device, comprising:
    a shaft member having an imaging lumen extending longitudinally therein;
    at least one cable extending through the imaging lumen, the at least one cable including:
        at least one conductor extending longitudinally through the imaging lumen for transmitting electronic data, and
        an insulating sheath surrounding the at least one conductor;
    a conductive wire having an exposed outer surface in the imaging lumen; and
    a shielding catheter extending along the shaft member, wherein the shielding catheter is disposed within the shaft member and surrounds a circumference of the imaging lumen, wherein the shielding catheter is electrically grounded, and wherein the shielding catheter and the conductive wire are connected to a same ground.

11. The medical device of claim 10, wherein the shielding catheter and the conductive wire are electrically coupled via connection of the shielding catheter and the conductive wire to the same ground.

12. The medical device of claim 10, wherein the same ground includes a floating ground, a signal ground, or an earth ground.

13. The medical device of claim 10, further comprising an irrigation lumen and an illumination lumen, and wherein the shielding catheter surrounds the irrigation lumen and the illumination lumen.

14. The medical device of claim 10, wherein the shielding catheter includes a braided catheter or a mesh catheter.

15. A medical device, comprising:
    a shaft member having an imaging lumen, a working lumen, an irrigation lumen, and an illumination lumen extending longitudinally therein;
    at least one cable extending through the imaging lumen, the at least one cable including:
        at least one conductor extending longitudinally through the imaging lumen for transmitting electronic data, and
        an insulating sheath surrounding the at least one conductor; and
    a braid disposed entirely within the shaft member and surrounding the imaging lumen, the working lumen, the irrigation lumen, and the illumination lumen, the braid providing electromagnetic interference shielding to the at least one cable.

16. The medical device of claim 15, wherein the braid is connected to a ground.

17. The medical device of claim 15, further comprising a conductive wire extending within the imaging lumen adjacent the at least one cable.

18. The medical device of claim 17, wherein the conductive wire lies between the at least one cable and the working lumen.

19. The medical device of claim 17, wherein a conductor of the conductive wire is exposed to the at least one cable and contacts an outer surface of the insulating sheath of the at least one cable.

* * * * *